United States Patent [19]

Orzalesi et al.

[11] 4,082,707

[45] Apr. 4, 1978

[54] 2-(4-ISOBUTYLPHENYL)-PROPIOHYDROXAMIC ACID AND A PROCEDURE FOR ITS PREPARATION

[75] Inventors: Giovanni Orzalesi; Renato Selleri, both of Florence, Italy

[73] Assignee: Societa Italo-Britannica L. Manetti-H. Roberts & Co., Florence, Italy

[21] Appl. No.: 735,525

[22] Filed: Oct. 26, 1976

Related U.S. Application Data

[63] Continuation of Ser. No. 428,835, Dec. 27, 1973, abandoned.

[30] Foreign Application Priority Data

Jan. 8, 1973 Italy .............................. 47550 A/73
Jul. 5, 1973 Italy .............................. 51249 A/73

[51] Int. Cl.$^2$ ............................................ C07C 83/10
[52] U.S. Cl. ............................ 260/500.5 H; 424/315
[58] Field of Search ............................ 260/500.5 H

[56] References Cited

U.S. PATENT DOCUMENTS

| | | | |
|---|---|---|---|
| 3,479,396 | 11/1969 | Buu-Hoi et al. | 260/500.5 H |
| 3,586,713 | 6/1971 | Buu-Hoi et al. | 260/500.5 H |
| 3,801,628 | 4/1974 | Vincent et al. | 260/500.5 H |
| 3,821,289 | 6/1974 | Diamond | 260/500.5 H |
| 3,828,093 | 8/1974 | Bays et al. | 260/500.5 H |

Primary Examiner—Joseph E. Evans

[57] ABSTRACT

The object of the invention is a new chemical compound 2-(4- isobutylphenyl)propiohydroxamic acid, having valuable analgesic, antipyretic and antiinflammatory properties, and a procedure for its synthesis.

1 Claim, No Drawings

2-(4-ISOBUTYLPHENYL)-PROPIOHYDROXAMIC ACID AND A PROCEDURE FOR ITS PREPARATION

This is a continuation of application Ser. No. 428,835, filed Dec. 27, 1973 and now abandoned.

The compound of the invention is chemically defined as 2-(4-isobutylphenyl)-propriohydroxamic acid and corresponds to the formula $C_{13}H_{19}NO_2$ which is represented by the following structure:

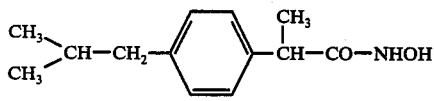

Its molecur weight is 221.3 Centesimal elementary analysis of the compound:

C 70.55 (found 70.11)
H 8.65 (found 9.02)
N 6.33 (found 6.15)
O 14.46 (by difference)

The compound appears as a crystalline solid in the shape of white shiny laminar scales, which are soluble in methanol, ethanol, acetone and ethyl ether, insoluble in water and petroleum ether. As it will also be indicated in the following, it crystallizes from acetone - petroleum ether and in this case it melts at 119° - 121° C on Kofler's hot stage.

Chromatographic analysis: on a thin $SiO_2$ layer (marketed under the trade name Merck GF254) Mobile phase: acetic acid-benzene-ethyl ether-methanol (in the ratios 18-120-60-1): result: a unitary stain visible in U.V. light of 254 mµ wavelength with Rfr~0.6.

One process for the preparation of the compound is the following:

2,3g of 2-(4-isobutylphenyl)-propionic acid, a compound which is well known and described in chemical literature) are solved in absolute ethanol, and 0.5ml. concentrated sulphuric acid is added thereafter. The whole is reflux heated for 4 hours and the reaction mixture is concentrated under reduced pressure. An oily residue is obtained which is cold treated with a saturated aqueous $NaHCO_3$ solution until its effervescence has disappeared. This latter treatment is performed by small successive additions. The obtained solution is extracted three times, with 50ml ethyl ether at a time. The etheric extracts are added together, dried on $MgSO_4$ and evaporated. Thus an oily residue is obtained which weights approximately 2.1g and consists of the ethyl ester of the starting acid. This ester is used such as it is in the further process.

To a solution of sodium methylate consisting of 0.5g Na in 15ml anhydrous methanol there is added a solution of 0.7g hydroxylamine hydrochlorate in 10ml. anhydrous methanol. It is filtered from the precipitated NaCl and to this mixture the precedently prepared 2.1g of ethyl ester is added. The whole is reflux heated for 15 minutes, cooled, slighly acidified with a 20% HCl solution, washed with water and finally with petroleum ether; it is crystallized from acetone/petroleum ether, to yield approximately 1g of the desired product. As already stated, it appears in the shape of white, shiny laminar scales, and has a melting point of 119-121° C on Kofler's hot stage.

A second process for the synthesis of the compound is the following:

Adding, under stirring and cooling, a solution of potassium hydroxide in methanol to a solution of hydroxylamine hydrochlorate in methanol and precipitating the potassium chloride; adding to said mixture, under continued stirring and cooling, an ethyl ether solution of 2-(4-isobutylphenyl)-propionic acid; suction filtering this mixture and washing the residue with methanol; putting together the methanol used for the washing and the filtrate and evaporating the whole at a reduced pressure; acidifying the resulting concentrated solution, letting it stand, suction filtering it; taking up the residue in petroleum ether and filtering again, thus obtaining the desired acid.

A purely illustrative and in no way limitative example of this second process will now be described:

In a 1000 ml three-necked flask equipped with a stirrer, a dropping funnel and a silica gel guard pipe, 46.7g hydroxylamine hydrochlorate are dissolved cold in 480 ml methanol. Separately a solution of 56.1g KOH in 280ml methanol is prepared, heated to 30° C and admixed dropwise under stirring to the hydroxylamine solution. All successive temperature increases during this admixture are prevented by cooling in an ice bath. After the whole KOH solution has been admixed, the mixture is left standing for 5 min. so as to attain the complete precipitation of the KCl.

Separately, 72.02g ethyl 2-(4-isobutylphenyl)-propionate, obtained by the esterification of 2-(4-isobutylphenyl)-propionic acid with ethanol and concentrated $H_2SO_4$, are solved with 100ml methanol, this solution is introduced drop by drop into the reaction flask, and stirred and cooled for 5 hours on an ice bath. Thereafter it is suction filtered, the residue is washed with alltogether 50ml methanol, the wash is added to the filtrate, thereafter the whole is evaporated in a water bath with a rotating evaporator at a reduced pressure, until 100–200 ml of a concentrated solution are obtained. This solution is poured into a 200 ml beaker into which are stirred approximately 1000 ml 1,25N acetic acid. This mixture is left standing for 24 hours, thereafter suction filtered. The resulting filtrate is taken up with 100ml. petroleum ether at 40°–60° C, in order to solve any possible residue of unreacted starting ester, and refiltered. Approximately 50g of 2-(4-isobutylphenyl)-propriohydroxamic acid are obtained, having a melting point of 119°–121° C on Kofler's hot stage.

As stated, the 2-(4-isobutylphenyl)-propriohydroxamic acid has marked analgesic, antipyretic and antiinflammatory properties.

Its analgesic property has been assessed
a. by the method of abdominal contractions according to Witkin et al. - 1. Pharmacol. exp. Ther., 1961, 133,400;
b. by the method of Randall L. O. and Selitto I. I. - Arch. Int. Pharmacodyn., 1957, 111, 409–419.

a. Method of Abdominal Contractions

These contractions were set off in male Swiss mice, weighing 22±2g and fasted for 18h, with water ad libitum, by i.p. injection of 0.1 ml/10g of a 3% (v/v) acetic acid solution. The 2-(4-isobutylphenyl)-propiohydroxamine acid, which for brevity will be termed G.277 forthwith, was administered per os, in dosages of 50, 100 and 200mg/kg body weight, 30 min. before the acetic acid injection. The contraction count was performed for 25 min., while neglecting the contractions recorded in the first 3 min., with the blind method. Groups of 10 animals each were used.

b. Method of Randall and Selitto

In male Wistar rats weighing 150±10g, fasted for 18h with water ad libitum, inflammation was caused by injecting 0.1 ml of a 20% aqueous yeast solution into the plantar region of the left hind paw.

The pain threshold has been measured by determining the pressure in grams which, when applied to the paw, caused the defensive reaction of the rat. This threshold was measured in the inflamed paw, as well as on the uninflamed ones, 1, 2, 3 and 4 hours after the oral administration of G277.

Antipyretic Properties

The antipyretic effect (Adams S.S., Hepborn P. et Nicholson I.S. - I. Pharmacol., 1968, 20, 305–312) was evalued on male Wistar rats weighing 200±10g, fasted for 18 hours with water ad libitum, in which hyperthermia was caused by subcutaneous injections of 2g/kg yeast in a 20% aqueous solution (corresponding to 1ml suspension per 100g bodyweight) 6 hours before starting the test.

The temperature was checked 1h10min. before the yeast injection, 10 min. before and 1, 2 and 3 hours before the administration of the G.277. Groups of 8 rats were used.

Antiinflammatory Properties

The antiinflammatory effect was assessed on male Wistar rats weighing 150±10g, fasted for 18 hours with water ad libitum, in whose hind leg an edema was induced by injecting into its plantar region the following edemigenous agents:

a. Dextran (Courvoisier S., Ducrot R.- Arch. Int. Pharmacodym., 1955, 102,33): 0.1 ml of a 3% dextran solution, 30 min. after the administration of G.277;

b. Formalin (Northover B. I. et Subramanian G., -Brit.I. Pharmacol. 1961, 16, 163): 0.1 ml of a 3% solution in 0.9% NaCl (physiologic solution), 1 hour before the oral administration of G.277;

c. 5-hydroxy-tryptamine (Parratt I.R. et West G.B.- Brit. I. Pharmacol., 1958, 13,65): 0.1 ml of a 5mg/ml (weight/vol.) solution in a 0.9% NaCl solution (physiologic solution), 30 min. after the oral administration of the G.277.

d. Carrageenin (Winter C.A., Risley E.A. et Nuss G.W. - Proc. Soc. exp. Biol. Med., 1962, III, 544–547) - 0.1 ml of a 1% solution, I hour after the oral administration of G.277.

Tests were also made using smaller doses of G.277: in this case the edema was induced 1 hour prior to the oral administration of G.277.

The intensity of the edema was measured by the "Basile" type differential volume measuring instrument for 3 hours from the injection of the edemigenous agents (for 3 hours from the administration of the product in case the G.277 had been administered after the formation of the edema). Groups of 8 animals each were used for these tests.

Toxicity

The DL 50 has been determined both intraparenterally and per os on male an female Swiss mice of 20±2g weight and on male and female Wistar rats of 150±10g weight. The control of the general conditions of the animals has been carried out for seven days from the treatment.

The DL 50 has been computed using the probit analysis (Luigi Cavalli Sforza — Statistical analysis for physicians and biologists — Publishers: Boringhieri — Turin, 1961.

Additionally subacute toxicity was determined by subjecting male Wistar rats of 150±10g weight for 20 days to a continuous treatment, on dosages of 25-50-100-300 mg/kg/day per os.

Comparison Compound

In all tests the G.277 was assessed in comparison with 2-(4-isobutylphenyl)-propionic acid (a compound which as stated is already known and well described in chemical literature) at idential dosages in mg/kg. Both were administered per os in a 2% gum arabic suspension. Results of the pharmacological tests:

I° The toxicity of G.277 administered parenterally is of the same order as that of the comparison compound, and ranges between 400 and 650 mg/kg. In oral administration the toxicity of G.277 is appreciably lower than that of the comparison compound and exceeds 2 and 3g/kg respectively in the mice and the rats.

II° The analysis of the intensity of the effect as a function of the time interval between administration of the compounds and the measurement of the effect, proves that the G.277 acts more readily than the comparison compound. This observation has been made concordantly in the antipyresis tests as well in that on analgesia according to the Randall and Selitto method and in that on the edema of the paw.

In human treatment three different dosages of G.277 are foreseen viz. 200, 250 and 300 mg. These dosages may be administered either orally, in the form of pellets, gelatine capsules or sugar coated dragees, or rectally, in the form of suppositories.

What is claimed is:

1. The compound 2-(4-isobutylphenyl)-propriohydroxamic acid having the structural formula

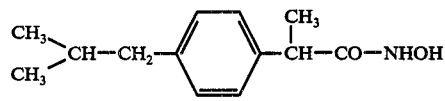

* * * * *